(12) United States Patent
Lysko et al.

(10) Patent No.: US 6,255,298 B1
(45) Date of Patent: Jul. 3, 2001

(54) MACROPHAGE SCAVENGER RECEPTOR ANTAGONISTS FOR USE IN THE TREATMENT OF CARDIOVASCULAR DISEASES

(75) Inventors: Paul G. Lysko, Downingtown; Joseph Weinstock, Wayne, both of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/463,863
(22) PCT Filed: Aug. 6, 1998
(86) PCT No.: PCT/US98/16374
  § 371 Date: Jan. 28, 2000
  § 102(e) Date: Jan. 28, 2000
(87) PCT Pub. No.: WO99/07382
  PCT Pub. Date: Feb. 18, 1999

Related U.S. Application Data

(60) Provisional application No. 60/055,397, filed on Aug. 6, 1997.

(51) Int. Cl.[7] ................................................ A61K 31/615
(52) U.S. Cl. ............................................................. 514/166
(58) Field of Search ............................................... 514/166

(56) References Cited

PUBLICATIONS

Database DWPI, week 197322, London;Derwent Publications Ltd., AN(1973)–3064OU, Class B05, DE 2254478 A (Miles Lab Inc.), Abstract.

Olin et al. Facts and Comparisons. St. Louis, MO:J.B. Lippincott. 1989, pp. 158–158k.

*Primary Examiner*—Raymond Henley, III
(74) *Attorney, Agent, or Firm*—Soma G. Simon; William T. King; Charles M. Kinzig

(57) ABSTRACT

Salicylanilide derivatives which are macrophagescavenger receptor antagonists are provided. Methods of treating cardiovascular disease comprising administration of the present compounds are also provided. The present compounds inhibit lipid accumulation within macrophage-derived foam cells.

10 Claims, No Drawings

MACROPHAGE SCAVENGER RECEPTOR ANTAGONISTS FOR USE IN THE TREATMENT OF CARDIOVASCULAR DISEASES

This is a 371 of PCT/US98/16374 filed Aug. 6, 1998 which claim proirity to U.S. provisional application Ser. No. 60/055,397 filed Aug. 6, 1997.

FIELD OF INVENTION

Cardiovascular diseases are the leading cause of death in the U.S., accounting annually for more than one million deaths. Atherosclerosis is the major contributor to coronary heart disease and a primary cause of non-accidental death in Western societies. Since the prevention of atherosclerosis is an enormous unmet medical need, considerable effort has been made in defining the etiology and potential treatment of atherosclerosis and its consequences, including myocardial infarction, angina, organ failure and stroke. Despite this effort, there are many unanswered questions including how and when atherosclerotic lesions become life-threatening, the best point of intervention, and how to detect and monitor the progression of lesions.

There is widespread agreement that multiple risk factors contribute to atherosclerosis including hypertension. elevated total serum cholesterol, high levels of low density lipoprotein ("LDL") cholesterol, low levels of high density lipoprotein ("HDL") cholesterol, diabetes mellitus. severe obesity, and cigarette smoking. To date, treatment of atherosclerosis has been narrowly focused on treating elevated cholesterol levels and modifying lipids has become the major focus of treatment and research.

However, recent studies have indicated that 40% of deaths due to coronary disease occurred in men with total cholesterol levels of below 220 mg/dl. It is thus obvious that too great an emphasis is being placed on lipid lowering. Indeed, only 30% of patients with atherosclerosis have elevated lipid levels, indicating that other pathogenic factors are involved. A logical scenario for future therapies and preventive measures should therefore include a multidisciplinary approach consisting of diet modification, HMG-CoA reductase inhibition and novel therapies aimed directly at plaque growth and stability.

The initial lesion in atherosclerosis is the fatty streak, which arises from cholesterol esters maintained as lipid droplets inside macrophage-derived foam cells. Macrophages down-regulate their LDL receptors and instead express mRNA and undergo new protein synthesis for a novel receptor for modified LDL. This receptor recognizes all modified forms of low-density lipoprotein and has come to be known as the macrophage scavenger receptor ("MSR"). If the macrophage is present in an environment that is continually generating modified LDL, it will accumulate lipid droplets of cholesterol esters, continuing until the macrophage dies from its toxic lipid burden. The released lipid then forms the a cellular necrotic core of the atherosclerotic lesion. Subsequent recruitment of fibroblasts, vascular smooth muscle cells and circulating monocytes and T-lymphocytes complete the inflammatory response and formation of the mature atherosclerotic plaque. Macrophage-derived foam cells are concentrated in the shoulders of plaques, where their secreted proteases and collagenases may contribute to plaque rupture which may lead to a fatal thrombotic event.

Plaque regression, a function of the dynamic balance among initiation, progression, stabilization and removal of plaque constituents, has been unequivocally demonstrated in humans as well as in numerous animal models. Multiple regression studies in non-human primates have shown that even relatively advanced lesions regress over time when atherogenic dietary stimuli are discontinued or pharmacological regimens are initiated.

Inhibition of lipid accumulation within macrophage-derived foam cells by utilizing MSR antagonists is expected to prevent plaque initiation, retard plaque progression, and initiate plaque regression through the process of "reversed cholesterol transport" to acceptor HDL. Thus, MSR antagonists provide a unique approach towards the pharmacotherapy of cardiovascular diseases such as atherosclerosis, coronary artery disease, renal disease, thrombosis, transient ischemia due to clotting, stroke, myocardial infarction, organ transplant, organ failure, and hypercholesterolemia.

SUMMARY OF THE INVENTION

The present invention involves salicylanilide derivatives represented by formula (I) hereinbelow and their use as macrophage scavenger receptor ("MSR") antagonists which are useful in the treatment of a variety of cardiovascular diseases including but not limited to atherosclerosis, coronary artery disease, renal disease, thrombosis, transient ischemia due to clotting, stroke, myocardial infarction, organ transplant, organ failure and hypercholesterolemia.

The present invention further provides methods for antagonizing the macrophage scavenger receptor in animals, including humans, comprising administering to an animal in need of treatment an effective amount of a compound of Formula (I), indicated hereinbelow.

The present invention further provides methods of inhibiting lipid accumulation within macrophage-derived foam cells.

DETAILED DESCRIPTION OF THE INVENTION

The compounds of the present invention are selected from Formula (I) hereinbelow:

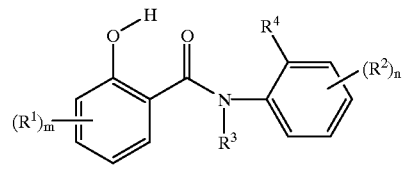

Formula (I)

wherein
  $R^1$ is independently selected from the group consisting of hydrogen, fluoroalkyl, halo, haloaryl, aryl, and alkoxy; or $R^1$ represents a fused ring forming a naphthalene moiety with the six membered aryl ring it substitutes;
  m is an integer from 1 to 4;
  $R^2$ is independently selected from the group consisting of $R^1$-benzamido, $R^1$-benzyl ether, $R^1$-benzylamino, amino, halo, hydroxy, alkoxy, alkyl, fluoroalkyl, cyano, nitro, aryloxy, nitroalkyl, aryl, and 1,2-benzo; or the $R^2$ moiety represents a fused ring forming a napthalene ring with the six membered aryl ring it substitutes;
  n is an integer from 1 to 4;
  $R^3$ is hydrogen or methyl; and
  $R^4$ is hydrogen or hydroxy.
  Preferably, $R^1$ is selected from the group consisting of hydrogen, 5-trifluoromethyl, 5-chloro, 5-bromo, 3-bromo, 4-bromo, 5-bromo-3-phenyl, 5-iodo, 5-iodo-3-phenyl, 2-phenyl, 3-phenyl, 5-phenyl and 3-methoxy.

More preferably, $R^1$ is 5-trifluoromethyl or 5-bromo.

Preferably, any $R^2$ aryl substituents are selected from the group consisting of hydroxy, halo, aryl, alkyl, cyano, nitro, $R^1$-benzamidyl, alkoxy and aryloxy. More preferably, $R^2$ is selected from the group consisting of 2-chloro, 3,4-dichloro, 2,3-dichloro, 3-methoxy, 2-isopropyl, 3-cyano, 4-butyl, 2-nitro, 2-phenoxy, 2-nitro-4-methyl, 2-phenyl, 4-phenyl, 2-benzamidyl, 1,2-benzo.

Most preferably, $R^2$ is 3,4-dichloro, 2-benzamidyl, 4-phenyl or 4-butyl.

Preferably, $R^3$ is hydrogen.

Particularly preferred compounds useful in the present invention include:

5-bromo-3',4'-dichlorosalicylanilide;

5-bromo-2'-amino-4',5'-dichiorosalicylanilide;

5-trifluoromethyl-4'-phenyisalicylanilide;

5-bromo-3'bromo-6'-hydroxysalicylanilide;

5-bromo-2'-benzamidyl-3',4'-dichlorosalicylanilide and 5-bromo-4'-bromosalicylanilide.

The present compounds can also be formulated as pharmaceutically acceptable salts and complexes thereof. Pharmaceutically acceptable salts are non-toxic salts in the amounts and concentrations at which they are administered.

Pharmaceutically acceptable salts for use when basic groups are present include acid addition salts such as those containing sulfate. hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present.

The present invention provides compounds of Formula (I) above which can be prepared using standard techniques. An overall strategy for preparing preferred compounds described herein can be carried out as described in this section. The examples which follow illustrate the synthesis of specific compounds. Using the protocols described herein as a model, one of ordinary skill in the art can readily produce other compounds of the present invention.

Scheme 1

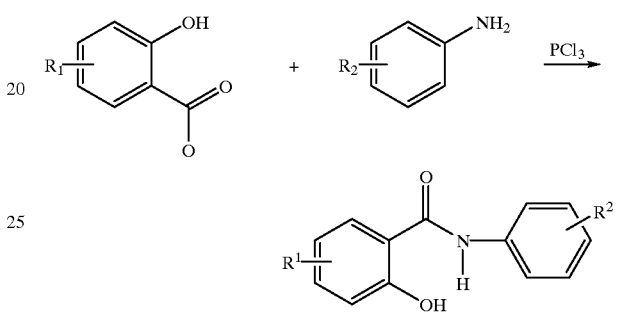

Salicylanilides may be prepared by heating a salicylic acid and aniline in the presence of phosphorus trichloride. A convenient procedure is to reflux the reactants in chlorobenzene as described by Lemaire, Schramm and Cahn, *Journal of Pharmaceutical Sciences*, 1961, Vol. 50, pp. 831–837, incorporated herein in its entirety by reference.

Salicylanilides may also be prepared using solid phase organic synthesis by the method indicated in Scheme 2, below. As used herein, the encircled "R" depicts a polymer solid support.

Scheme 2

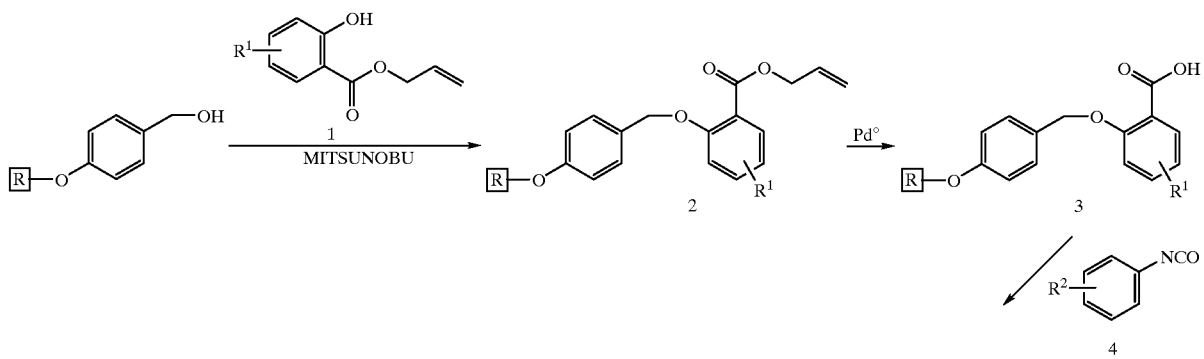

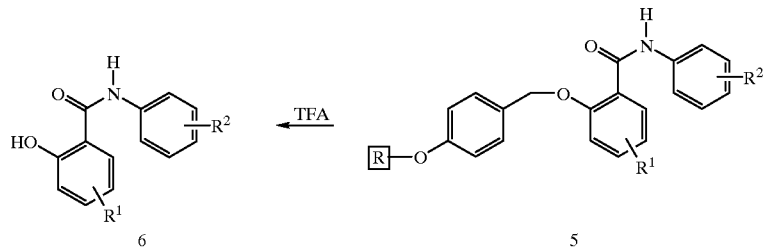

In the following synthetic examples, temperature is in degrees Celsius (° C.). Unless otherwise indicated, all of the starting materials were obtained from commercial sources. Without further elaboration, it is believed that one skilled in the art can, using the description provided in this specification, utilize the present invention to its fullest extent. These Examples are given to illustrate the invention, not to limit its scope. Reference is made to the claims for what is reserved to the inventors hereunder.

EXAMPLE 1

5-Bromo-3'4'-dichlorosalicylanilide

A slurry of 5-bromosalicylic acid (15 g, 69 mmol) and 3,4-dichloroaniline (19.85 g, 73 mmol) and phosphorous trichloride (4.74 g 34.5 mmol) in 300 ml of chlorobenzene was refluxed for 3 hr. The hot solution was filtered through a glasswool plug and allowed to stand at room temperature for 18 hr. The crystals which deposited were collected by filtration and washed with fresh chlorobenzene and then methylene chloride to give after drying 19 g (76%) of product mp 230–233°. HPLC $t_r$ 19.25 min (Vydac HS5215 C18 ODS, 2.1×150 mm, 0.2 mL/min, gradient, A: water–0.1% trifluoroacetic acid B: acetonitrile–0.1% trifluoroacetic acid, 90–10% A during 20 min, UV detection at 214 nm). Recrystallization from chlorobenzene and then acetone gave 11.5 g of crystals, mp 237–2380°. The structure was verified by X-ray crystallography.

EXAMPLE 2

5-Trifluoromethyl-4'-phenylsalicylanilide

Phosphorous trichloride (0.70g, 5.1 mmol) was added to a mixture of 4-trifluoromethylsalicylic acid and 4-aminobiphenyl in 30 ml of chlorobenzene. The mixture was refluxed for 3.5 hr and a solid collected by filtration of the hot mixture. A second crop was obtained by filtering the cold filtrate. This was triturated with $CH_2Cl_2$ and the solid collected by filtration and washed with fresh $CH_2Cl_2$. Elemental analysis (C,H,N) was correct for $C_{20}H_{14}F_3NO_2 \cdot \frac{1}{2}H_2O$.

EXAMPLE 3

5-Bromo-3'4'-dichlorosalicylamide by Solid Phase Organic Synthesis a) Preparation of Allyl 5-bromosalicylate (1-Scheme 2)

A mixture of 5-bromosalicylic acid (10 g, 46 mmol), allyl bromide (6.12 g, 51 mmol) and sodium bicarbonate (4.65 g, 55 mmol) in 50 ml of DMF was stirred under a drying tube for 72 hr. The reaction mixture was poured into water, extracted with ethyl acetate. and the organic layer dried over $MgSO_4$. Concentration under vacuum gave 10.73 g (91%) of product (1-Scheme 2) with the expected NMR.

b) Coupling of Allyl 5-bromosalicylate to Wang Resin (2-Scheme 2)

Wang resin (1.7 mmol per gram functionality) (0.358 g, 0.61 mmol), allyl 5-bromosalicylate (1-Scheme 2), (0.79 g, 3.08 mmol), tributylphosphine (2.46 mmol) and 1,1'-azobis (N,N-dimethylformide) (0.424 g, 2.46 mmol) in a mixture of 10 ml of chloroform and 10 ml of tetrahydrofuran was shaken under argon for 18 hr. The reaction solvent was removed and the resin washed with $THF/CH_2Cl_2$ (1:1, 3 times). $CH_2Cl_2$ (3 times), THF (3 times), and $CH_2Cl_2$ (3 times). Drying gave 0.485 g (95%) of the theoretical weight gain. FTIR showed and magic angle NMR showed the anticipated peaks.

c) 5-Bromosalicylic Acid on Wan Resin (3-Scheme 2)

A suspension of 0.200 g of 2-Scheme 1 and 60 mg of tetrakis (triphenylphosphine)-paladium (0) in 15 ml of a mixture of $CH_2Cl_2$, morpholine and water (100:10:2) was shaken under argon for 72 hr. After removal of the reaction solution the resin was washed with $CH_2Cl_2$ (3 times), DMF-water (1:1, 3 times), DMF (2 times), dioxane (3 times), dioxane-2% HOAc (1:1, 3 times), dioxane-water (1:1, 3 times), dioxane (4 times) and $CH_2Cl_2$ (4 times). Drying gave 0.2 g of resin-bound intermediate 3-Scheme 1. Magic angle and NMR showed the loss of the allyl group.

d) 5-Bromo-3'4',-dichlorosalicylanilide (6-Scheme 2)

A suspension of 21.6 mg (0.0287 mmol) of 3-Scheme 1), 57 mg (0.287 mmol) of 3,4-dichlorophenyl isocyanate, 4-Scheme 1, 0.75 ml of triethylamine, and 10 ml of toluene was heated at 70° C. under argon for 18 hr. The reaction solution was removed and the resin washed 3 times with DMF, 3 times with dioxane and 3 times with $CH_2Cl_2$. A sample was treated with a solution of $CH_2Cl_2$-TFA-triethylsilane (5:5:0.5) for 2 hr to release the product from the resin. HPLC analysis (Vydac C18, 15 cm by 2.1 mm column, flow rate 0.2 ml per min., acetonitrile-methanol gradient: 40% acetonitrile for 4 min., gradient to 90% over 8 min., hold 4 min., gradient to 100% methanol over 2 min.) showed major anilide with minor 5-bromosalicylic acid.

With appropriate manipulation and protection of any chemical functionality, synthesis of the remaining compounds of Formula (I) is accomplished by methods analogous to those above and to those described in the Experimental section.

In order to use a compound of Formula (I) or a pharmaceutically acceptable salt thereof for the treatment of humans and other mammals, it is normally formulated in accordance with standard pharmaceutical practice as a pharmaceutical composition.

The present compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous, For injection, the compounds of the invention are formulated in liquid solutions, preferably, in physiologically compatible buffers or solutions, such as saline solution, Hank's solution, or Ringer's solution. In addition, the compounds may be formulated in solid form and re-dissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered.

Preferably the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg. and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 to 100 mg/Kg, of a compound of Formula (I). A topical formulation contains suitably 0.01 to 5.0% of a compound of Formula (I). The active ingredient may be administered from 1 to 6 times per day, preferably once, sufficient to exhibit the desired activity, as is readily apparent to one skilled in the art.

As used herein, "treatment" of a disease includes, but is not limited to prevention, retardation and prophylaxis of the disease.

The MSR receptors described in the present application belong to a recently classified group designated the SR-A group and exist in two forms, type A-I and type A-II, which arise through differential exon splicing of a single gene. The terms "MSR" and "SR-A" are used interchangeably in the present application.

Diseases and disorders which might be treated or prevented, based upon the affected cells, include atherosclerosis, coronary artery disease, renal disease, thrombosis, transient ischemia during clotting, stroke, organ transplant, organ failure, myocardial infarction and hypercholesterolemia.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil. olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene giycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

The biological activity of the compounds of Formula (I) are demonstrated by the following tests.

Assays of MSR activity, both degradation and binding/internalization, were adapted from Goldstein et al., "Receptor-mediated Endocytosis of Low-density Lipoprotein in cultured Cells," *Methods Enzymol.*, 98:241–260 (1983); incorporated herein in its entirety by reference. Briefly, 293 cells transfected with MSRI or II are seeded at $10^5$ cells/ml/well in a 24-well dish in Eagle's Minimal Essential Medium with 2 mM glutamine, 10% FCS and 0.4 mg/ml geneticin. After 2 days, the medium is replaced with 500µl fresh serum-free medium containing 2 mg/ml BSA and 125[I]-AcLDL (iodinated acetylated low density lipoprotein) at 5 µg/ml, and cells are incubated at 37C for 5 hours. After this suitable period for ligand degradation, cells are removed to a 4C cold room. Supernatant is removed into trichloroacetic acid, and the mixture is centrifuged. The supernatant is chloroform-extracted in order to isolate 125 [I]-monoiodotyrosine, the degradation product of 125[I]-AcLDL, and portions are counted to determine degradative activity. To determine cell-associated ligand, cell monolayers are washed and incubated at 4C with ice-cold buffer "A" containing 150 mM NaCl, 50 mM Tris-HCl, and 2 mg/ml BSA, pH 7.4, to eliminate nonspecifically bound counts.

Cells are washed three times rapidly with 1 ml, incubated twice for 10 min each on a rotary shaker in 1 ml buffer A, then washed twice rapidly in 1 ml buffer A without BSA. After aspiration of all wash buffer, cells are lysed in 0.1N NaOH and removed to counting vials for determination of binding/uptake and subsequent protein determination (Pierce BCA protein assay). The present actives yield $IC_{50}$ values of <50 um in degradation assays and <100 um in binding/uptake assays.

The fluorescent compound DiI-AcLDL (1,1'-dioctadecyl-3,3,3',3'-tetramethylindocarbocyanine perchlorate-labeled LDL) has also been shown to be a useful tool in assessing activity of the macrophage scavenger receptor (Freeman et al., *Proc. Natl. Acad. Sci., USA*, 88:4931–4935 (1991); Penman et al., *J. Biol. Chem.*, 266:23985–23993 (1991)). We also utilized an assay for MSR antagonists based on the uptake of DiI-AcLDL by the transfected HEK 293 cells. For most assays, HEK 293 cells transfected with SR-AI were used, although both SR-AI and SR-AII appeared to have equivalent activity in all studies performed. Briefly, HEK 293 cells were seeded at $2 \times 10^4$ cells/well in a 96-well plate in EMEM with 2 mM glutamine, 10% FBS and 0.4 mg/ml geneticin. The assay was standardized and optimized, and testing was performed in serum-free EMEM containing 2 mg/ml bovine serum albumin. Confluent cells were incubated with DiI-AcLDL (final concentration 2 ug/ml) in the absence and presence of inhibitors (quadruplicate wells) for 4 hours at 37C. Following aspiration of solution and a Locke's buffer wash, results were quantified with a fluorescence plate reader at 530nm exc/590 nm em.

All publications, including but not limited to patents and patent applications cited in this specification are herein incorporated by reference as if each individual publication were specifically and individually indicated to be incorporated by reference as though fully set forth.

What is claimed is:

1. A method of treating a cardiovascular disease or condition which comprises administering to a subject in need of treatment an effective amount of a compound having the structure of Formula (I):

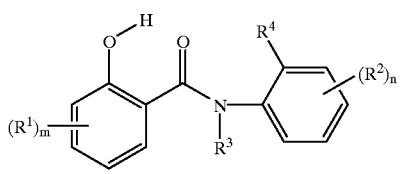

Formula (I)

wherein: $R^1$ is independently selected from the group consisting of hydrogen, fluoroalkyl, halo, haloaryl, aryl, and alkoxy; or $R^1$ represents a fused ring forming a naphthalene moiety with the six membered aryl ring it substitutes;

m is an integer from 1 to 4;

$R^2$ is independently selected from the group consisting of $R^1$-benzamido, $R^1$-benzyl ether, $R^1$-benzylamino, amino, halo, hydroxy, alkoxy, alkyl, fluoroalkyl, cyano, nitro, aryloxy, nitroalkyl, aryl, and 1,2-benzo; or the $R^2$ moiety represents a fused ring forming a napthalene ring with the six membered aryl ring it substitutes;

n is an integer from 1 to 4;

$R^3$ is hydrogen or methyl; and $R^4$ is hydrogen or hydroxy.

2. A method according to claim 1 wherein:

$R^1$ is selected from the group consisting of hydrogen, 5-trifluoromethyl, 5-chloro, 5-bromo, 3-bromo, 4-bromo, 5-bromo-3-phenyl, 5-iodo, 5-iodo-3-phenyl, 2-phenyl, 3-phenyl, 5-phenyl and 3-methoxy;

$R^2$ is selected from the group consisting of 2-chloro, 3,4-dichloro, 2,3-dichloro, 3-methoxy, 2-isopropyl, 3-cyano, 4-butyl, 2-nitro, 2-phenoxy, 2-nitro-4-methyl, 2-phenyl, 4-phenyl, 2-benzamidyl, 1,2-benzo; and $R^3$ is hydrogen.

3. A method according to claim 1 wherein any $R^2$ aryl substituents are selected from the group consisting of hydroxy, halo, aryl, alkyl, cyano, nitro, $R^1$-benzamidyl, alkoxy and aryloxy.

4. A method according to claim 2 wherein $R^2$ is selected from 3,4-dichloro, 2-benzamidyl, 4-phenyl or 4-butyl.

5. A method according to claim 2 wherein $R^1$ is 5-trifluoromethyl or 5-bromo.

6. A method according to claim 1 wherein the compound is selected from the group consisting of:

5-bromo-3',4'-dichlorosalicylanilide;

5-bromo-2'-amino-4',5'-dichlorosalicylanilide;

5-trifluoromethyl-4'-phenylsalicylanilide;

5-bromo-3'bromo-6'-hydroxysalicylanilide;

5-bromo-2'-benzamidyl-3',4'-dichlorosalicylanilide and 5-bromo-4'-bromosalicylanilide.

7. A method according to claim 1 wherein the disease or disorder is selected from the group consisting of atherosclerosis, coronary artery disease, renal disease, thrombosis, transient ischemia due to clotting, organ transplant, organ failure, stroke, myocardial infarction and hypercholesterolemia.

8. A method according to claim 7 wherein the disease or disorder being treated is atherosclerosis.

9. A method of antagonizing a macrophage scavenger receptor comprising administering to a subject in need of treatment an effective amount of a compound having the structure of Formula (I):

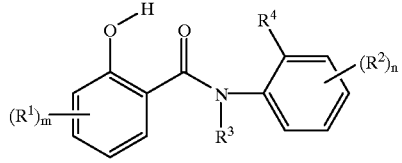

Formula (I)

wherein: $R^1$ is independently selected from the group consisting of hydrogen, fluoroalkyl, halo, haloaryl, aryl, and alkoxy; or $R^1$ represents a fused ring forming a naphthalene moiety with the six membered aryl ring it substitutes;

m is an integer from 1 to 4;

$R^2$ is independently selected from the group consisting of $R^1$-benzamido, $R^1$-benzyl ether, $R^1$-benzylamino, amino, halo, hydroxy, alkoxy, alkyl, fluoroalkyl, cyano, nitro, aryloxy, nitroalkyl, aryl, and 1,2-benzo; or the $R^2$ moiety represents a fused ring forming a napthalene ring with the six membered aryl ring it substitutes;

n is an integer from 1 to 4;

$R^3$ is hydrogen or methyl; and $R^4$ is hydrogen or hydroxy.

10. A method of inhibiting lipid accumulation within macrophage-derived foam cells by administering to a subject in need of treatment an effective amount of a compound having the structure of Formula (I)

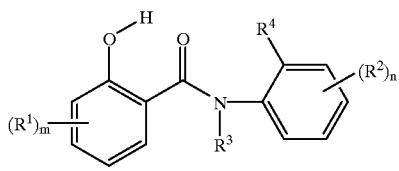

Formula (I)

wherein: $R^1$ is independently selected from the group consisting of hydrogen, fluoroalkyl, halo, haloaryl, aryl, and alkoxy; or $R^1$ represents a fused ring forming a naphthalene moiety with the six membered aryl ring it substitutes;

m is an integer from 1 to 4;

$R^2$ is independently selected from the group consisting of $R^1$-benzamido, $R^1$-benzyl ether, $R^1$-benzylamino, amino, halo, hydroxy, alkoxy, alkyl, fluoroalkyl, cyano, nitro, aryloxy, nitroalkyl, aryl, and 1,2-benzo; or the $R^2$ moiety represents a fused ring forming a napthalene ring with the six membered aryl ring it substitutes;

n is an integer from 1 to 4;

$R^3$ is hydrogen or methyl; and $R^4$ is hydrogen or hydroxy.

* * * * *